(12) United States Patent  (10) Patent No.: US 9,250,167 B2
Pasternak et al.  (45) Date of Patent: Feb. 2, 2016

(54) MOLD AND MOLDING APPARATUS FOR EMBEDDING BIOLOGICAL SPECIMEN IN A BLOCK AND RELATED METHODS

(71) Applicant: UC-CARE LTD., Yokneam (IL)

(72) Inventors: Alex Pasternak, Tel Aviv (IL); Keren Schweizer, Tal El (IL)

(73) Assignee: UC-CARE LTD., Yokneam (IL)

( * ) Notice: Subject to any disclaimer, the term of this patent is extended or adjusted under 35 U.S.C. 154(b) by 0 days.

(21) Appl. No.: 14/377,854

(22) PCT Filed: Dec. 17, 2013

(86) PCT No.: PCT/IL2013/051038
§ 371 (c)(1),
(2) Date: Aug. 10, 2014

(87) PCT Pub. No.: WO2014/097295
PCT Pub. Date: Jun. 26, 2014

(65) Prior Publication Data
US 2015/0008616 A1    Jan. 8, 2015

Related U.S. Application Data

(60) Provisional application No. 61/737,845, filed on Dec. 17, 2012, provisional application No. 61/905,296, filed on Nov. 18, 2013.

(51) Int. Cl.
*B29C 39/10* (2006.01)
*G01N 1/36* (2006.01)
*B29B 13/00* (2006.01)

(52) U.S. Cl.
CPC *G01N 1/36* (2013.01); *B29B 13/00* (2013.01); *G01N 2001/366* (2013.01)

(58) Field of Classification Search
None
See application file for complete search history.

(56) References Cited

U.S. PATENT DOCUMENTS

| | | | | |
|---|---|---|---|---|
| 4,023,308 | A * | 5/1977 | Staby | 47/79 |
| 4,549,670 | A * | 10/1985 | Trendler | 422/536 |
| 5,269,671 | A * | 12/1993 | McCormick | 425/117 |
| 5,612,218 | A | 3/1997 | Busch et al. | |
| 5,968,436 | A * | 10/1999 | Takezaki | 264/250 |
| 6,395,234 | B1 * | 5/2002 | Hunnell et al. | 422/554 |
| 7,156,814 | B1 | 1/2007 | Williamson, IV | |
| 8,329,120 | B2 * | 12/2012 | Williamson et al. | 422/536 |
| 2010/0184127 | A1 * | 7/2010 | Williamson et al. | 435/40.52 |

FOREIGN PATENT DOCUMENTS

GB   2144366   *  3/1985
WO   2013/105095    7/2013

* cited by examiner

*Primary Examiner* — Edmund Lee
(74) *Attorney, Agent, or Firm* — Roach Brown McCarthy & Gruber, P.C.; Kevin D. McCarthy

(57) ABSTRACT

A mold for producing a biological tissue embedded in a block of an embedding material is provided. The mold comprises a compartment having a compartment floor and a depression extending downwards from the compartment floor. A molding apparatus, comprising a mold and a press for pressing a sample sheet onto the compartment floor of the mold is provided. The press comprises a foot configured to enter at least partially into the compartment and press a sample tissue, at least partially into the depression. A method of embedding a biological tissue in an embedding material using a mold as described herein is provided. A cleaning device configured for removing excess embedding materials from the press of the molding apparatus is provided.

23 Claims, 10 Drawing Sheets

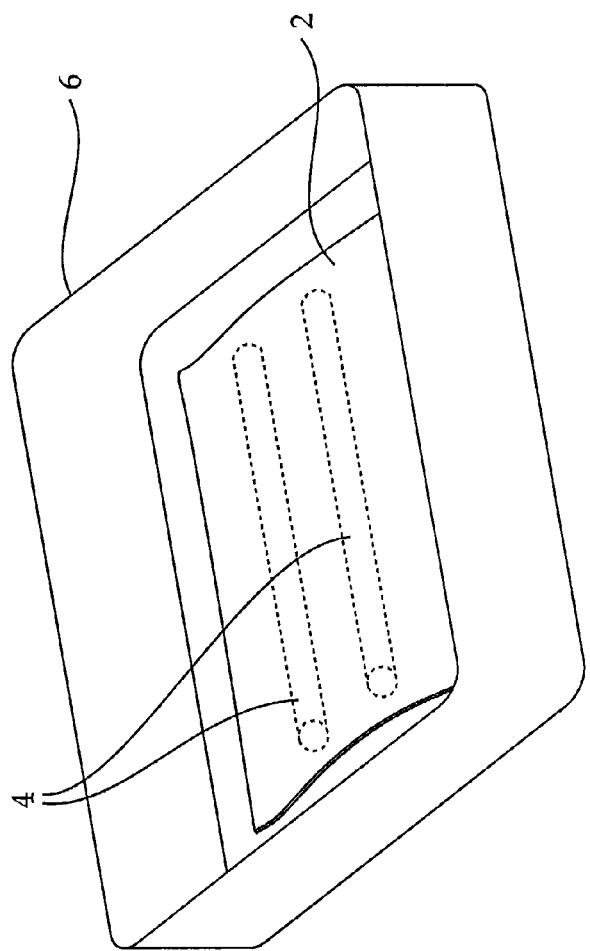
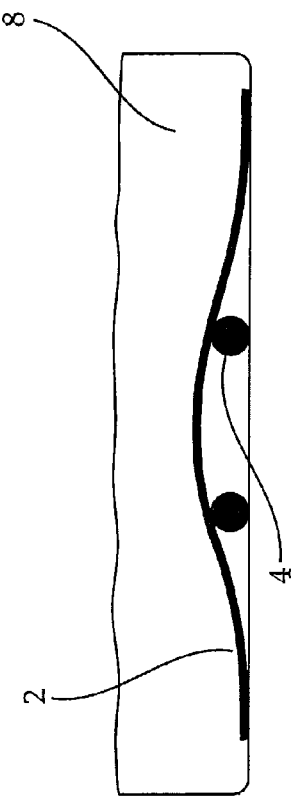
FIGURE 1A (prior art)
FIGURE 1B (prior art)

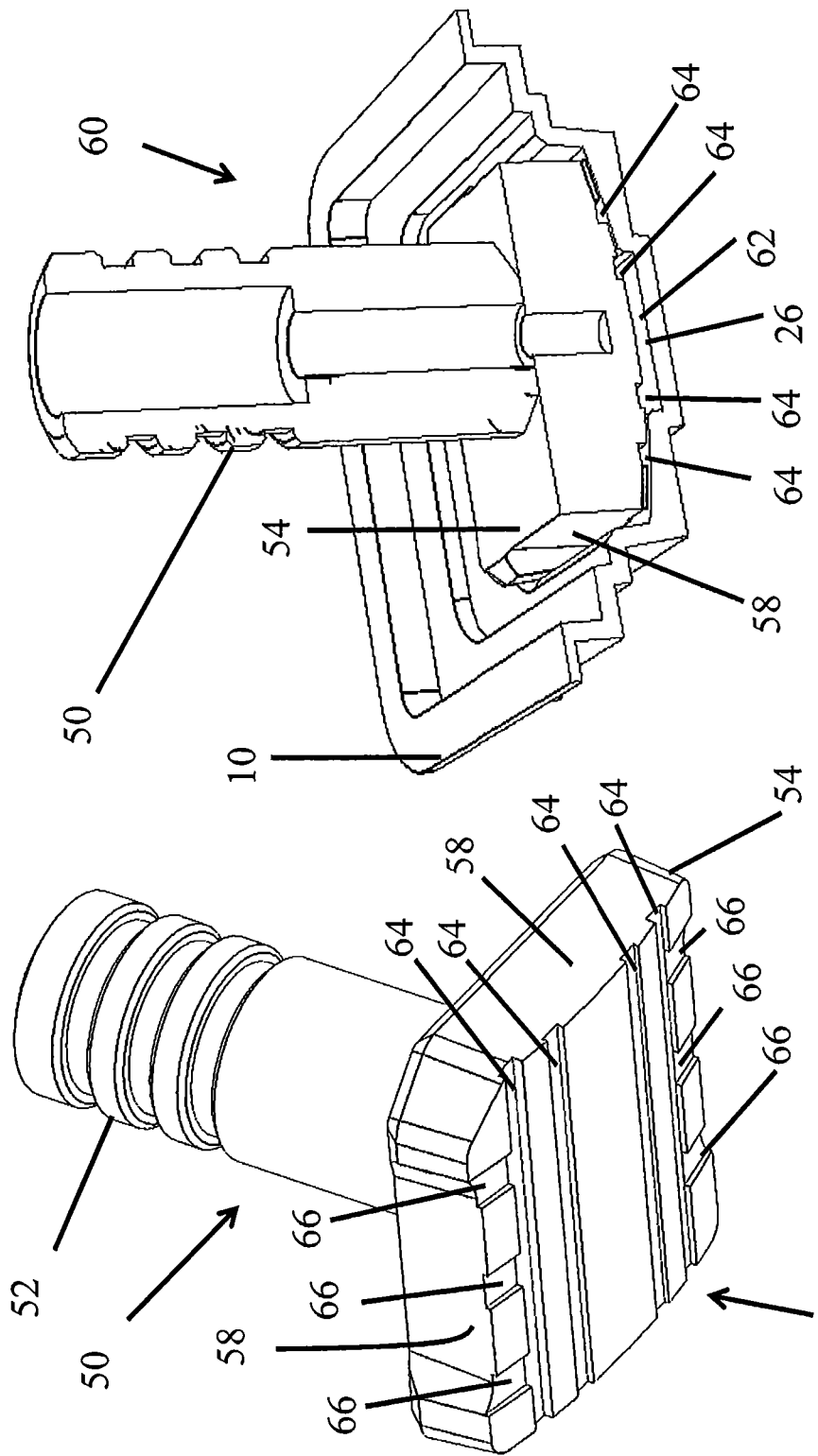

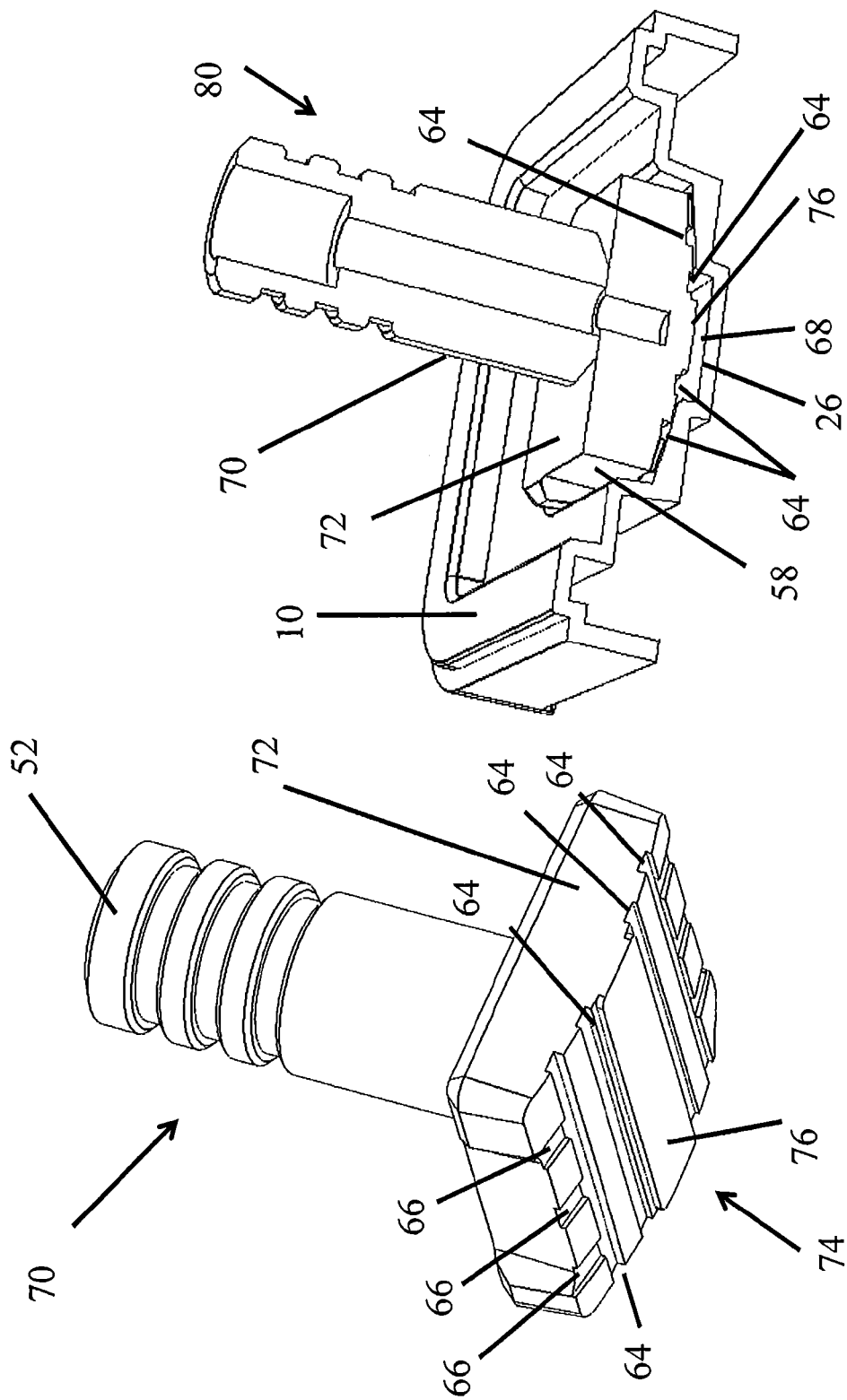

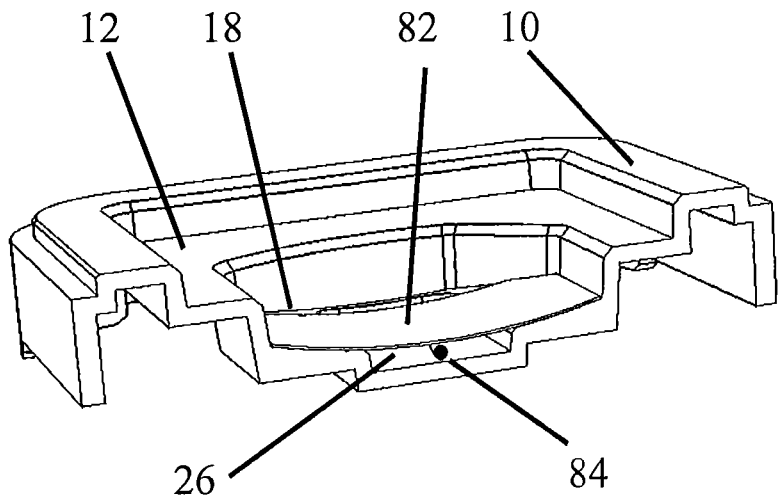
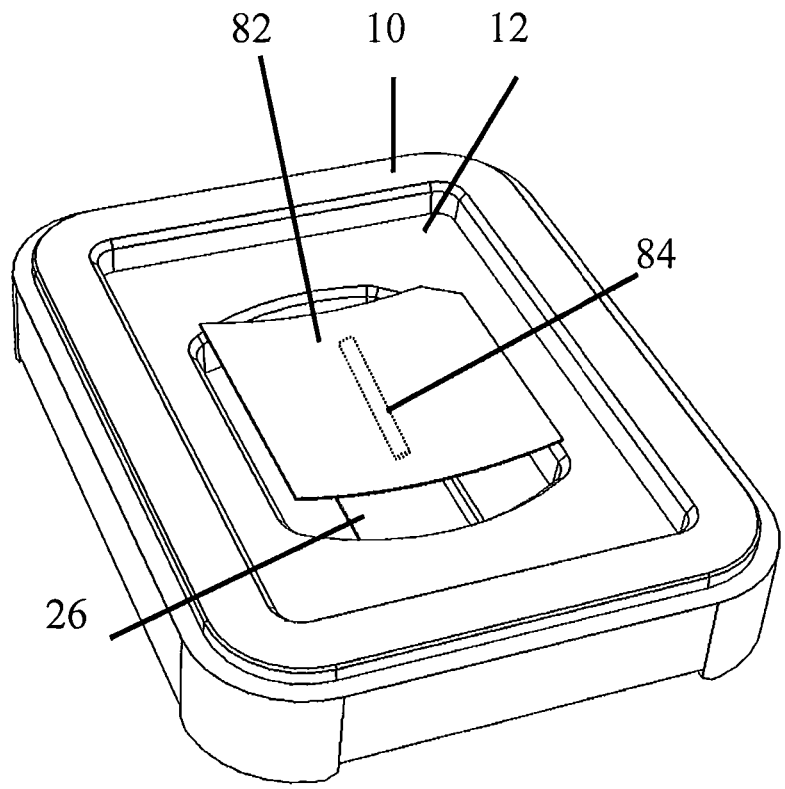

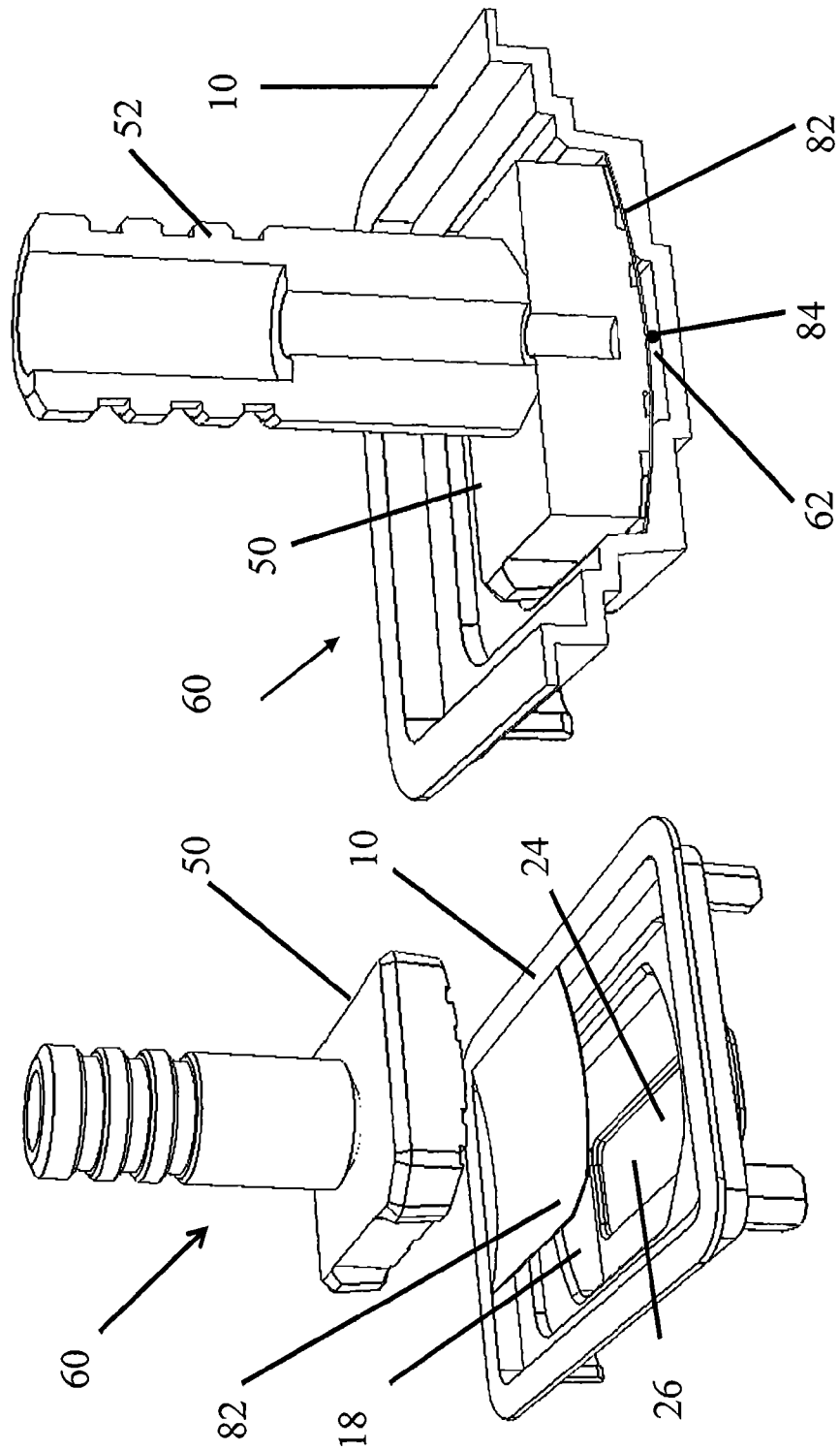

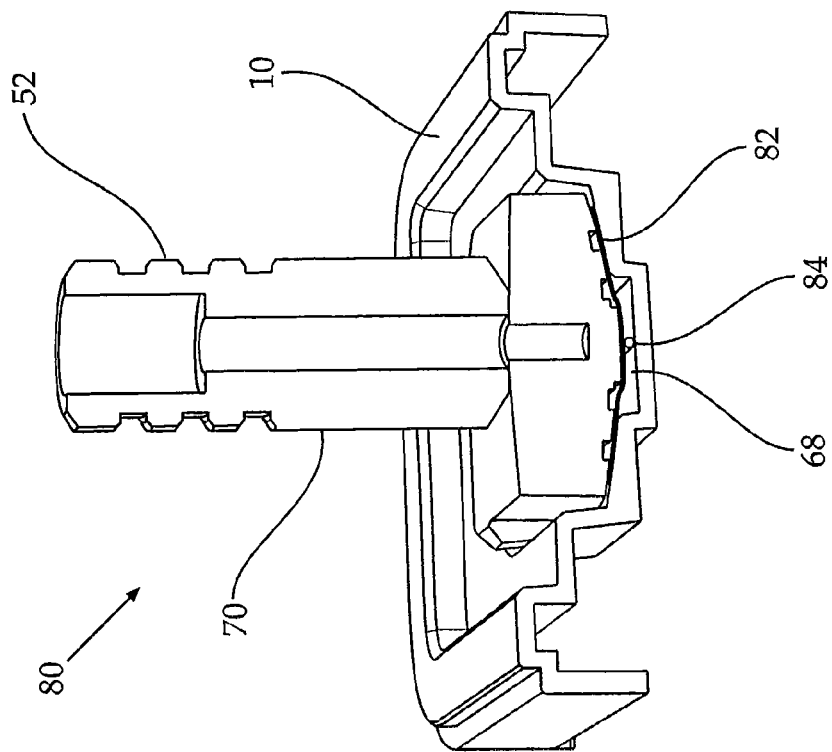
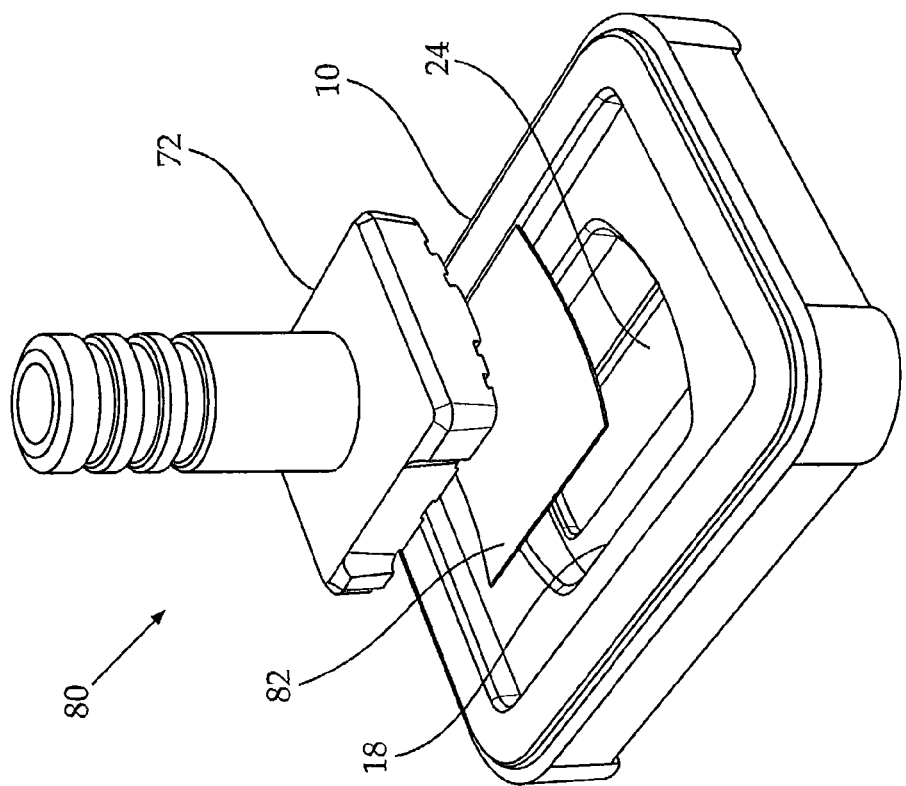

MOLD AND MOLDING APPARATUS FOR EMBEDDING BIOLOGICAL SPECIMEN IN A BLOCK AND RELATED METHODS

RELATED APPLICATION DATA

The present application is a U.S. National Stage application of International Application PCT/IL2013/051038, filed on Dec. 17, 2013 by the inventors of the present application and titled: "MOLD AND MOLDING APPARATUS FOR EMBEDDING BIOLOGICAL SPECIMEN IN A BLOCK AND RELATED METHODS"; International Application PCT/IL2013/051038 claims the benefit of US Provisional Application No. 61/737,845 filed on Dec. 17, 2012; and International Application PCT/IL2013/051038 claims the benefit of US Provisional Application No. 61/905,296, filed on Nov. 18, 2013; all of the aforementioned applications are hereby incorporated herein by reference in their entirety.

FIELD OF THE INVENTION

The invention, in some embodiments, relates to the field of molds and molding apparatuses for embedding a biological specimen in a block of embedding material, and more particularly but not exclusively, to molds and molding apparatuses for embedding a biopsy sample in a block of embedding material prior to sectioning.

BACKGROUND OF THE INVENTION

Molds are often used during processing of biological specimen e.g. for fixing such specimen in a block of an embedding material. For example, molds, typically made of stainless steel, are used for embedding samples of biopsy tissues in a paraffin block. Such embedding is carried out as a preliminary step before sectioning the samples for examining the tissues e.g. under a microscope in a histopathology laboratory.

Biopsy tissues may be obtained from a live organ using one of various methods. The following description relates to obtaining and processing core biopsy tissues for histopathology; however relevant steps of the method described below are commonly employed for preparation of other types of biopsy tissues as well.

Core biopsy is a routine procedure used to obtain a sample of a biological tissue using a core biopsy needle. The obtained sample tissue has a typical shape of a long and narrow stripe—e.g. about 20 mm long and about 1 mm wide. A typical preparation process of a core biopsy sample prior to examination is detailed for example in U.S. Pat. No. 7,156,814, and may include the following steps:

a. The biological sample is placed in a sample box, possibly after being submerged in a preservative solution. Inside the sample box the sample is gently pressed, using a box cover, between two sheets of a soft material such as a sponge, which prevents displacement of the sample tissue inside the box. An example of a sample box is Tissue-Tek® Uni-Cassettes® by SAKURA FINETEK USA, INC. The sample box is then marked with an alpha-numeric string (e.g. digits and letters) identifying the sample and its origin.

b. The tissue inside the box may be taken through a chemical process, possibly of several hours, intended to fixate and dry the sample. The chemical process may include immersion in neutral buffered formaldehyde preservative solution, in ethanol, in xylene and/or in paraffin. Then the sample tissue is dried.

c. Dried tissue is removed from the sample box and placed in a mold, the mold being about the size of the sample box. The sample tissue is fixed to the compartment floor of the mold, typically using a drop of liquid paraffin and by gently pressing onto the sample tissue until the paraffin solidifies. An example of a metal mold is Tissue-Tek® Compartment floor Molds by SAKURA FINETEK USA, INC.

d. The sample box, without cover, is fixed on top of the metal mold, and the space within, that is to say between the metal mold and the sample box, is filled with liquid paraffin.

e. After the block of paraffin solidifies the metal mold is removed, leaving the sample box (with the marked string identifying the sample tissue) filled with a block of paraffin and with the sample tissue on top.

f. The sample box with the sample tissue is taken for slicing. Slices of typical thickness of a few microns are taken from the top surface of the paraffin block, carrying slices of the sample tissue therein.

g. Selected slices are placed between two glass plates and inserted to an oven for melting the paraffin. After removing the liquid paraffin, the sample tissue between two glass plates is taken for examination, e.g. under a microscope.

U.S. Pat. No. 5,612,218 discloses a mould for embedding a tissue sample in a paraffin block, having a recess with a bottom. Provided in the bottom of the recess is a cavity whose cross-section corresponds substantially to the cross-section of the tissue sample.

Some methods for processing sample tissues include, prior to embedding the sample tissue in a block, attaching the sample tissue to a sample sheet. Some such methods are described in international patent application publication WO 2013/105095, filed on Jan. 10, 2013, which is incorporated herein by reference in its entirety. Such a sample sheet may adhere to a biological tissue upon manually pressing on, or adjoining the biological tissue and the sample sheet. Such a sample sheet can further maintain adherence with the biological tissue, and the biological tissue remains stuck to the sample sheet following immersion in water solutions such as formaldehyde and during a chemical process applied to the sample tissue in preparation to examination, as described above. Examples for a sample sheet as described herein include: a mesh film of cellulose esters such as Immobilon-NC Transfer Membrane by Millipore™; a film such as Mixed Cellulose Esters Membrane ME 25 or WME by Whatman Ltd; and a film such as Supor® 200 PES Membrane Disc Filter by Pall Corporation or NL-17 or Super charged membrane by Whatman Ltd. Further examples for a sample sheet may include a film such as Cellulose Filters, for example grade 1 or grade 42 or grade 542, by Whatman Ltd. Further examples for a sample sheet may include a mesh film of cellulose esters covered with glue or another adhesive material so that sample tissues adhere to it. Examples for a sample sheet may further include paper, or another thin and flexible sheet that may adhere to a sample tissue upon contact the sample tissue and the sample sheet or upon adjoining the sample tissue and the sample sheet, by glue, adhesive forces, electrostatic forces or using any other technique.

SUMMARY OF THE INVENTION

According to an aspect of some embodiments, the invention relates to the field of molds for embedding a biological specimen in a block of embedding material. According to some embodiments the invention relates to molds for embedding a biopsy sample in a block of embedding material prior to sectioning.

Current methods for handling a biopsy sample and particularly for embedding such a biopsy sample in a block of embedding material as discussed above may suffer significant deficiencies. Specifically, step (c) above including embedding the biopsy sample in a paraffin block, is carried out with relatively little control on the position, orientation and spatial arrangement of the sample tissue on the compartment floor of the mold. In practice, the sample tissue may curl, may partially lift from compartment floor or may even split to several pieces. A sample which is captured in the block in position or orientation which diverts from an ideal horizontal and straight arrangement might lead to a smaller sample size in a slice after sectioning the block, to loss of original orientation of the sample, and generally to reduced inspection efficiency and detection likelihood.

According to some methods and as discussed above, the sample tissue may be attached to the compartment floor of the mold, e.g. using a drop of liquid paraffin which solidifies quickly, and by pressing the sample onto the compartment floor during the solidification of the paraffin. Such pressing may be carried out e.g. by pressing the sample in multiple points thereon typically by hand and using a pointed tool. Such a method may be less than optimal, since an even pressure on the sample towards the compartment floor of the mold cannot be guaranteed. While pressing the sample in one side, another side may lift from the compartment floor. Further, points of the sample which are held pressed to the compartment floor as the paraffin solidifies might remain squeezed, while other regions of the sample are not squeezed, and may even be slightly detached from the compartment floor. Alternatively to pressing the sample using a pointed tool, a press having a flat, planar foot may be used. Ideally, such a press may compel and restrict the sample tissue to a plane, as substantially dictated by the planar foot of the press. Yet, in practice it is difficult if not impossible to employ a constant force by hand when pressing various samples in various occasions. Moreover, even if constant force may be guaranteed, the pressure on a particular sample is dependent on the sample's surface size. Further yet, even if constant pressure could be guaranteed, the amount of squeezing of a particular sample may depend on the stiffness of the sample. Consequently, when using a planar press, some samples may be too squeezed towards the compartment floor, whereas other samples may be insufficiently pressed. Moreover when using a press to manually press samples onto a mold's compartment floor, deviations from parallelism between the compartment floor and the planar foot of the press may not be completely avoided. As a result a sample may be pressed more on one side and therefore squeezed too much on that one side, and may be pressed less, or not at all, on another side.

Some methods for processing sample tissues include, prior to embedding the sample tissue in a block, attaching the sample tissue to a sample sheet. Such methods may further include placing the sample in a mold so that the sample tissue is on a surface of the sample sheet facing the compartment floor of the mold. FIG. 1A schematically illustrates a sample sheet 2 carrying two core biopsy samples 6, positioned in a mold 6 so that the biopsy samples are disposed between the sample sheet and the compartment floor of the mold. According to such methods, another step may include employing an embedding material to form a block of the embedding material inside the mold that captures and embeds the sample sheet there inside with the biological sample. FIG. 1B schematically depicts, in a cross-sectional view, a block of an embedding material 8, embedding sample sheet 2 and core biopsy samples 4.

Generally, employing a sample sheet as described above to facilitate handling a sample tissue in a process such as a process of preparation for examination is preferred over alternative methods that do not employ such a sample sheet. Particularly, a sample tissue that is adhered to a sample sheet and placed inside a mold usually maintains its shape, and therefore maintains straightness and planarity. By using such a sample sheet, loss of specimen, particularly loss of small portions thereof which are otherwise lost, is prevented or at least minimized Further, basic handling functions such as carrying the sample from place to place are simplified.

Yet, if a sample sheet holding a sample tissue as described above is placed on a planar compartment floor of a mold, the produced block of embedding material incorporating the sample tissue and the sample sheet may be less than optimal. Particularly, portions of the sample sheet that are not supported by the sample tissue may fold down, as schematically depicted in FIG. 1A and in FIG. 1B. As a result, segments of the sample sheet may be situated in planes of sectioning of the block of paraffin for obtaining slices of the sample tissue, and obstruct or jeopardize the sectioning.

Thus, according to an aspect of some embodiments, there is provided a mold for producing a biological tissue embedded in a block of an embedding material. The mold comprises a compartment configured for containing the embedding material, and the compartment comprises a compartment floor and at least one wall extending upwards from the compartment floor. The compartment further comprises at least one depression extending downwards from the compartment floor, wherein the depression comprises a depression floor. At least one of the depression floor and compartment floor is curved at least along one direction, thereby being centrally inclined. The depression is configured for accepting a biological tissue at least partially therein. The mold is thereby configured for producing a block of an embedding material having at least one protrusion associated with the at least one depression, wherein the biological tissue is embedded at least partially in the protrusion.

According to some embodiments the depression has a non-symmetrical shape, substantially precluding rotational symmetry of the mold except for the trivial rotational symmetry of 360 degrees, so that the block of embedding material produced in the mold has a non-symmetrical shape, substantially precluding rotational symmetry of the block except for the trivial rotational symmetry of 360 degrees. A non-symmetrical block enables knowing and maintaining an orientation of a sample even when the sample is embedded inside the block. For example, a core biopsy sample may be placed in the mold so that a distal side of the core biopsy is closer to a particular side of the block. The particular side of the block may be recognized because of the lack of rotational symmetry, hence the orientation of the sample may be known even when the sample is embedded in the embedding material and even if the sample therefore may not be seen.

According to some embodiments, the compartment floor is non-planar. By non-planar compartment floor it is meant that the compartment floor is not flat, thus substantially diverging from a plane. According to some embodiments the compartment may have a first upper surface comprising with the compartment floor, and further comprise a step-wise depression extending downwards from the compartment floor and having a depression floor defining a second surface lower than the upper surface. According to some embodiments the depression may have a rectangular shape (in top view), having walls extending upwards from the floor of the depression towards the upper surface. According to some embodiments the compartment floor may be split by a single step, thus divided into an upper surface on one side and a depression on another side. According to some embodiments the compartment may have compartment floor consisting of a first upper surface, a step-wise depression extending downwards from the upper surface and a sample recess extending downwards from the floor of the depression, as is exemplified in FIGS. 2 and 3 herein. According to some embodiments the compartment may have a shape of a muffin-tin or an egg cartoon, having an array of depressions configured for accepting biological tissues therein. According to some embodiments the compartment floor may have a shape of an undulated sheet, thereby being configured for accepting a plurality of sample tissues having a long and narrow shape such as core biopsies. According to some embodiments, one or two or a plurality of samples may be placed in a single depression.

In some embodiments the compartment floor is centrally inclined or concave along one direction, thereby defining a downward slope in from the periphery of the compartment floor to its center along the one direction, as is described and explained below.

According to a further aspect of some embodiments the mold described above is configured to accept a sample sheet configured to attach to a biological tissue and hold the biological tissue thereon. The sample sheet is dimensioned to be positioned in the compartment and to be constrained to the position thereof, at least along one direction, by the compartment. According to some embodiments the sample sheet may be round and the compartment may constrain the position of the sample sheet by preventing the sample sheet from displacing laterally. According to some embodiments the sample sheet may have a non-round shape, e.g. a rectangular shape, and the compartment may constrain the position of the sample sheet by limiting rotations (in the horizontal plane) of the sample sheet. Constraining the position of the sample sheet is advantageous because it enables knowing the position of a sample tissue inside the block of embedding material, if the position of the sample tissue on the sample sheet is known.

According to some embodiments the a sample sheet carrying a sample tissue thereon may be positioned in the compartment of the mold, so that the biological tissue faces the floor of the depression and located at least partially within the depression in the compartment.

According to a further aspect of some embodiments there is provided a molding apparatus comprising the mold described above and a press. The molding apparatus is configured to enable employing the press to press a biological tissue onto the non-planar compartment floor, and at least partially into the depression. According to some embodiments the press has a non-planar foot surface fitting in shape, at least partially, to the compartment floor of the mold. In some embodiments the foot comprises a protrusion configured to enter at least partially into the depression, when the press is suitably pressed onto the compartment floor. According to some embodiments the foot comprises channels configured to drain excess embedding material from a region between the foot surface and the mold, when the press presses onto the mold and the mold contains liquid embedding material.

According to a further aspect of some embodiments there is provided a method of embedding a biological tissue in a block of an embedding material, comprising:
 providing a mold as described above;
 placing a biological tissue in the compartment and at least partially inside at least one depression, and
 employing an embedding material to produce a block of the embedding material inside the compartment wherein the biological tissue is embedded at least partially in a protrusion of the block corresponding to at least one depression of the compartment.

According to some embodiments the method further comprises the steps of:
 providing a sample sheet configured to attach to a biological tissue and hold the biological tissue thereon and is further dimensioned to be positioned in the compartment and to be constrained to the position thereof, at least along one direction, by the compartment;
 attaching a biological tissue to the sample sheet, and
 positioning the sample sheet having the biological tissue thereon inside the compartment so that the biological tissue faces the depression floor and located at least partially within the at least one depression of the compartment.

According to some embodiments the method further comprises the steps of:
 providing a press having a foot with a non-planar foot surface wherein the foot is configured to insert at least partially into the compartment of the mold; and
 pressing the press onto the compartment floor thereby inserting the biological tissue at least partially into the at least one depression, and thereby obtaining a block of the embedding material comprising the biological tissue embedded at least partially in the at least one protrusion of the block.

According to some embodiments the foot of the press is planar and flat. According to some embodiments the foot of the press is non-planar, comprising at least one protrusion configured to enter at least partially into at least one depression in the compartment floor, when the press is pressed onto the compartment floor. According to some embodiments the foot of the press is convex, having a similar curvature to a curvature of a concave non-planar portion of the compartment floor in the mold. According to some embodiments the foot of the press is convex as described above, and also comprises at least one protrusion configured to enter at least partially into at least one depression in the compartment floor, as described above. According to some embodiments, the foot of the press comprises channels such as grooves or tunnels or through-holes, the channels being configured to drain away excess embedding material from a region between the press and the mold during such pressing.

According to a further aspect of some embodiments there is provided a cleaning device for cleaning a press. The cleaning device is configured to heat the press e.g. by placing the press on a surface of the cleaning device, such that at least part of the embedding material attached to the press is melted or liquefied and thus removed from the press.

Aspects and embodiments of the invention are described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

FIG. 1A schematically depicts sample tissues adhered to a sample sheet inside a mold of the prior art;

FIG. 1B schematically depicts a cross-section view of a block of an embedding material embedding sample tissues adhered to a sample sheet, as produced using the mold of FIG. 1A;

FIG. 3A schematically depicts in a perspective bottom view an embodiment of a press for pressing a sample tissue onto a compartment floor of the mold of FIG. 2A;

FIG. 3B schematically depicts a cross-section of an embodiment of a molding apparatus comprising the mold of FIG. 2A and the press of FIG. 3A;

FIG. 4A schematically depicts in a perspective bottom view another embodiment of a press for pressing a sample tissue onto the compartment floor of the mold of FIG. 2A;

FIG. 4B schematically depicts a cross-section of an embodiment of a molding apparatus comprising the mold of FIG. 2A and the press of FIG. 4A;

FIGS. 5A and 5B schematically depict, in an exploded view and a cross-section view, respectively, the mold of FIG. 2A with a sample tissue adhered to a sample sheet, the sample sheet being positioned in the mold;

FIGS. 6A and 6B schematically depict, in an exploded view and a cross-section view, respectively, an embodiment of a molding apparatus comprising the mold of FIG. 2A and the press of FIG. 3A, in use with a sample sheet;

FIGS. 7A and 7B schematically depict, in an exploded view and a cross-section view, respectively, an embodiment of a molding apparatus comprising the mold of FIG. 2A and the press of FIG. 4A, in use with a sample sheet;

DESCRIPTION OF SOME EMBODIMENTS OF THE INVENTION

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

Figure 2A:
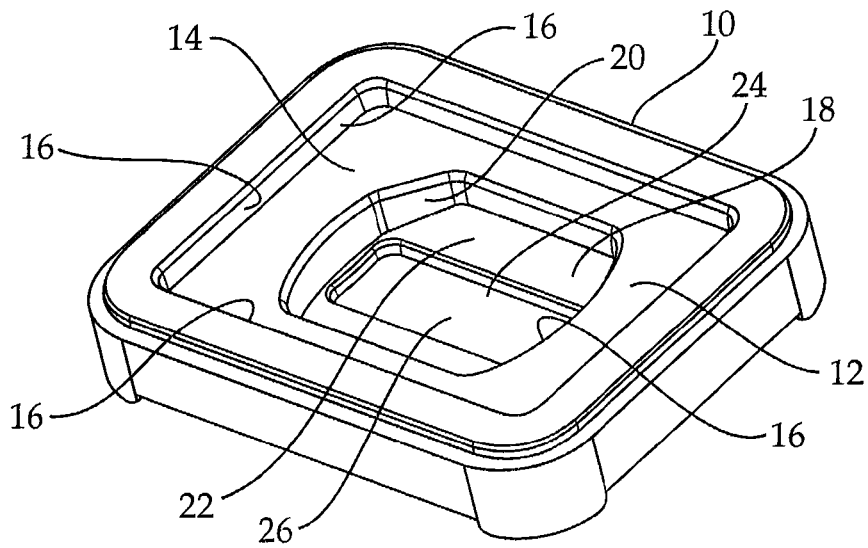
FIGS. 2A and 2B schematically depict an embodiment of a mold as described herein in perspective view and in cross section view respectively.
Figure 2B:
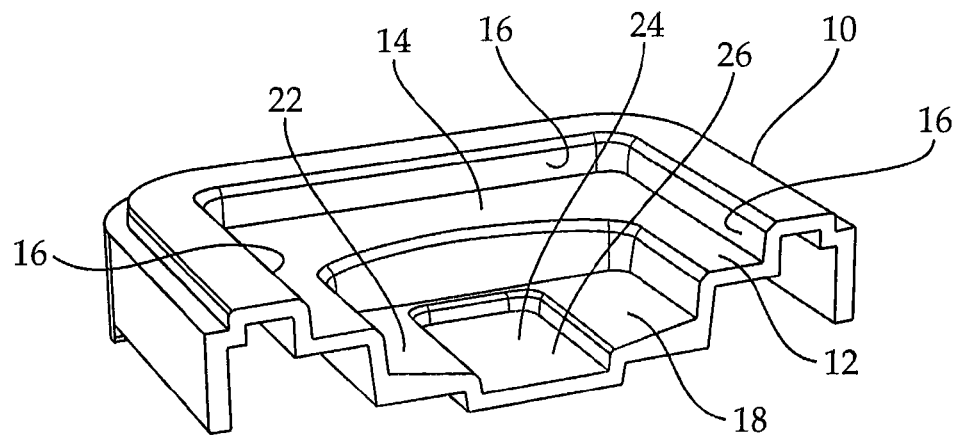

FIGS. 2A and 2B schematically depict an embodiment of a mold 10 in perspective view and in cross section view, respectively. Mold 10 is configured for producing a biological tissue embedded in a block of an embedding material, as is further explained in detail herein below. Mold 10 comprises a compartment 12 configured for containing the embedding material. For example, if paraffin is the embedding material, hot and liquid paraffin may be poured into compartment 12 and cooled therein until the paraffin solidifies to a block. Thus, compartment 12 defines a bottom part of the block's shape.

Compartment 12 comprises a non-planar compartment floor 14 confined by four walls 16 extending upwards from compartment floor 14. Compartment 12 comprises a sample sheet depression 18 configured to accept a sample sheet (not shown) holding a sample of a biological tissue thereon. The sample sheet depression may have in some embodiments a non-symmetrical shape (when viewed from the top). Sample sheet depression 18 comprises a single truncated corner 20, having thereby a generally rectangular shape with one truncated corner. By having a non-symmetrical shape, sample sheet depression precludes from mold 10 a rotational symmetry (except for the trivial 360 degrees rotation). According to some embodiments, a sample sheet used with mold 10 may have a non-symmetrical shape corresponding to a non-symmetrical shape of the sample sheet depression, thereby identifying an orientation. For example the sample sheet may have a rectangular shape having similar dimensions to dimensions of the sample sheet depression, and having one truncated corner corresponding to a truncated corner of the sample sheet depression. The sample sheet may thus be positioned inside the sample sheet depression in a single orientation only, thereby establishing an unambiguous relation between a shape of the block of embedded material produced in the mold, and an orientation of the sample sheet embedded therein.

Sample sheet depression 18 further comprises a depression floor 22 at a bottom thereof. A sample recess 24, extends downwards from sample depression floor 22 to a recess floor 26 on a bottom portion thereof. Sample recess 24 is configured to accept at least one biological sample, for example a core biopsy sample, obtained e.g. using a biopsy needle. Such a biological sample may be situated in sample recess 24 according to at least one of several methods, as is further described and explained below. According to some embodiments, one or two or a plurality of separate samples may be placed in sample recess 24.

Figure 2C:
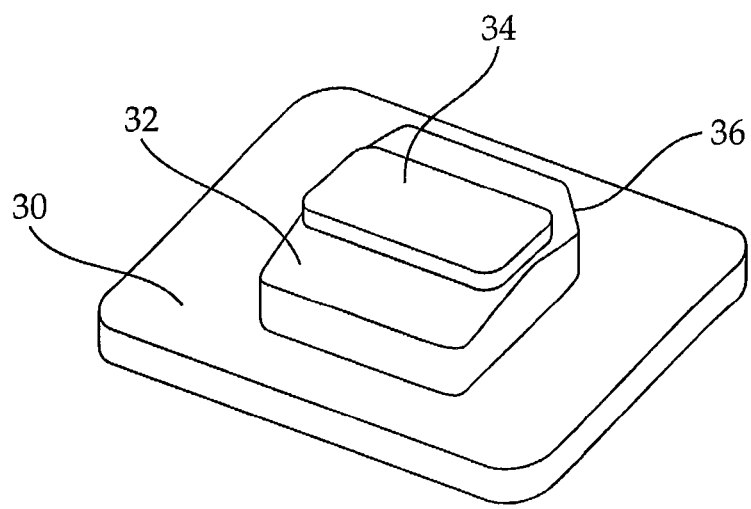
FIG. 2C schematically depicts a block of an embedding material that was produced in the mold of FIGS. 1A and 1B.

According to some embodiments, depression floor 22 is centrally-inclined, i.e. lower at its center then at its perimeter. Being centrally inclined means that the sample sheet depression has a downward slope in a direction from the periphery of the depression floor to its center, as is illustrated in FIG. 2B. Depression floor 22 is curved along the cross-section plain of FIG. 2B, so that depression floor 22 is lower near sample recess 24 compared to near the periphery of depression floor 22. In use, an embedding material may be employed with mold 10, having a biological sample in sample recess 24, to produce a block of an embedding material that captures the biological sample there inside. For example, a sample tissue may be placed inside sample recess 24 and hot and liquid paraffin may be then poured into compartment 12 until the paraffin covers the sample tissue and fills sample recess 24, sample sheet depression 18 and possibly a part of compartment 12 between four walls 16. In some embodiments such paraffin may be poured into mold 10 in two steps or even in more than two steps, wherein each step is performed after the paraffin poured in the previous step had solidified. After the paraffin cools and solidifies, a block of paraffin embedding the sample tissue is thereby produced. FIG. 2C depicts schematically a block 30 of an embedding material that was produced in mold 10 having a sample tissue in sample recess 24. Block 30 comprises a sample sheet protrusion 32 and sample protrusion 34, corresponding to sample sheet depression 18 and to sample recess 24 of mold 10, respectively. The sample tissue is, at least partially, inside sample protrusion 34.

Since depression floor 22 is centrally-inclined, i.e. lower towards its center (surrounding sample recess 24) then at its periphery, sample sheet protrusion 32 is convex. Further, sample sheet protrusion 32 comprises a truncated corner 36 corresponding to truncated corner 20 of sample sheet depression 18.

FIG. 3A schematically depicts from a perspective bottom view an embodiment of a press 50 for pressing a sample tissue onto compartment floor 14 of mold 10. Press 50 comprises a handle 52 for gripping and maneuvering press 50. Press 50 further comprises a foot 54, attached to handle 52. Foot 54 has outer dimensions that allow foot 54 to enter into sample sheet depression 18 in mold 10. Foot 54 comprises a foot surface 56 at the bottom of foot 54. Foot surface 56 is generally convex with a similar or a same curvature of depression floor 22, thereby coinciding with depression floor 22 at least along an areal portion thereof when foot 54 is entered into sample sheet depression 18.

FIG. 3B depicts schematically a cross-section of an embodiment of a molding apparatus 60 comprising press 50 and mold 10, when foot 54 is entered into sample sheet depression 18 of mold 10. A gap 62 exists between foot surface 56 and recess floor 26 in sample recess 24, wherein gap 62 is roughly equal to the depth of sample recess 24. When entered into sample sheet depression 18, press 50 may consequently constrain or press a sample tissue positioned in sample recess 24, as is further explained below Foot surface 56 comprises major channels 64 grooved along foot surface 56, for removing excess liquid embedding material from sample sheet depression 18 when foot 54 is pressed into sample sheet depression 18. Major channels 64 are at least partly open at foot surface 56 to drain liquid embedding material from foot surface 56 in a general direction from the center towards the perimeter of foot surface 56. Foot surface 56 further comprises minor channels 66, arranged perpendicular to major channels 64 and extending from major channels 64 towards the perimeter of foot 54 for removing embedding material from major channel 64. Minor channels 66 are at least partly open at major channel 64 to drain liquid embedding material from major channel 64. Foot 54 further comprises side depressions 58 along the perimeter of foot 54. When press 50 is pressed onto mold 10 and foot 54 is entered into sample sheet depression 18 containing liquid embedding material, excess embedding material draining through major channels 64 and minor channels 66 may further be released upwards through side depressions 58 and through the subsequent gaps between foot 54 and the walls of sample sheet depression 18. According to some embodiments major channels 64 may also comprise through holes in foot 54 extending from foot surface 56 upwards through the foot, thereby enabling draining liquid embedding material from the foot surface upwards through the through hole or through holes to above the foot.

FIG. 4A schematically depicts from a perspective bottom view an embodiment of a press 70 for pressing a sample tissue onto compartment floor 14 of mold 10. Press 70 comprises a foot 72 having a foot surface 74. Press 70 is different from press 50 in that foot 72 comprises a foot protrusion 76 protruding downwards from foot surface 74.

FIG. 4B depicts schematically a cross-section of an embodiment of a molding apparatus 80 comprising mold 10 and press 70. Foot 72 is entered into sample sheet depression 18, whereas foot protrusion 76 is entered into sample recess 24. Foot protrusion 76 substantially protrudes into sample recess 24, thus gap 68 between sample recess floor 26 and foot protrusion 76 in FIG. 4B is generally smaller than gap 62 between sample recess floor 26 and foot surface 56 in FIG. 3B.

For use of molding apparatus 60 or molding apparatus 80, a sample tissue may be positioned on sample recess floor 26 of mold 10 and liquid embedding material may be added to mold 10. Press 50 or press 70 may then be used for pressing the sample tissue onto sample recess floor 26. During pressing, liquid embedding material is present between sample recess 24 and foot surface 56 or foot surface 74, respectively. While a certain amount of embedding material is required to fill up sample recess 24 to form, following solidification, sample protrusion 34, any excess amount of embedding material may be removed by major channels 64 and/or minor channels 66 which drain any excess amount of embedding material.

According to some embodiments, gap 62 and gap 68 are configured to be large enough to include sample tissues therein without substantially squeezing such sample tissues. According to some embodiments, gap 62 and gap 68 are configured to be fit to sample tissues size, so that a typical sample tissue is pressed to floor 26 of compartment floor 14 by a pre-defined amount. For example when using molding apparatus 60 or molding apparatus 80 with core biopsy samples obtained using a core biopsy needle and having a typical width of 1 mm in diameter, gap 62 and/or gap 68 may be configured to have, according to some embodiments, a height of 1.3 mm, thereby constraining the sample to a maximum distance from a top of the sample protrusion of nominally 0.3 mm. According to some embodiments, gap 62 and/or gap 68 may be about 1 mm, thereby constraining the sample to sample recess floor 26 and consequently to the top of sample protrusion 34. According to some embodiments gap 62 and/or gap 68 may be 0.7 mm at the center axis, thereby squeezing a typical core biopsy sample by 0.3 mm.

The dimensions of gap 62 or gap 68 are determined by the type of mold and press used. For example, using a molding apparatus 60 as described in FIG. 3B defines gap 62 by sample recess floor 26, whereas the walls of sample recess 24 extend upwards from sample recess floor 26, and by a convex curve of foot surface 56. Likewise, using a molding apparatus 80 as described in FIG. 4B defines gap 68 by sample recess floor 26 and by foot protrusion 76.

According to some methods, molding apparatus 60 may be employed to embed a sample tissue in a block of an embedding material such as block 30 of FIG. 2C. For example, paraffin may be used as the embedding material as is explained below. A small amount of liquid paraffin, less than an amount required to fill sample recess 24, is poured into sample recess 24. A sample tissue is situated in sample recess 24 and press 50 is pressed into sample sheet depression 18, thereby pressing the sample tissue into sample recess 24 and submerging the sample tissue in the small amount of paraffin therein. After the small amount of paraffin solidifies, thereby capturing the sample tissue, press 50 may be removed, and an additional amount of liquid paraffin may be poured into compartment 12 to produce a complete block such as block 30.

Employing press 50 or press 70 as described above to press the sample tissue into sample recess 24 is advantageous because the eventual arrangement of the sample tissue inside block 30 is not dependent on the force applied on press 50. In other words, press 50 is pressed until foot surface 56 or foot surface 74, respectively, contacts depression floor 22, and therefore the sample tissue inside sample recess 24 is not squeezed or, alternatively, is squeezed to a pre-defined amount as described above. Consequently, when eventually the sample tissue is embedded in block 30, the sample tissue may be confined to a plane and parallel to sample recess floor 26 of sample recess 24, conforming to the general shape of the gap. Employing press 50 or press 70 as described above is further advantageous because major channels 64 and minor channels 66 drain excess paraffin from sample recess 24 outwards to the periphery region of depression floor 22 and possibly upwards through side depressions 58, thus enabling the press (whether press 50 or press 70) to press against sample sheet depression 18 without being stopped by the opposite pressure of such excess paraffin.

FIG. 5A is an exploded diagram schematically depicting a use of mold 10 with a sample sheet 82. Sample sheet 82 is configured to adhere to a sample tissue, substantially as described above. Sample sheet 82 is dimensioned to fit into sample sheet depression 18 in mold 10. According to some embodiments, a sample tissue 84 (an edge of which is shown in FIGS. 5A and 5B) may be adhered to sample sheet 82 on a face thereof facing sample recess floor 26 of sample recess 24. Sample sheet 82 is thus configured to be placed substantially inside sample sheet depression 18 so that sample tissue 84 is situated substantially inside sample recess 24.

FIG. 5B schematically depicts mold 10 and sample sheet 82 in cross-section view. Sample sheet 82 is situated inside sample sheet depression 18, and sample tissue 84 is thereby situated substantially within gap 62. According to some embodiments, a block of an embedding material such as block 30 and including a sample tissue adhered to sample sheet 82 there inside may be produced by employing the embedding material in conjunction with mold 10. For example, liquid paraffin may be poured into compartment 12 of mold 10. Sample sheet 82 and sample tissue 84 may be suitably arranged therein, prior to pouring the embedding material or after pouring the embedding material. After the paraffin solidifies a block embedding sample tissue 84 is thereby produced. According to some embodiments sample sheet 82 may be perforated or punctured or slotted, thereby being permeable to liquid paraffin, so that liquid paraffin may easily pour through sample sheet 82 to fill in sample recess 24.

According to some embodiments, mold 10 is advantageous because sample sheet 82 may not fold or flex, thus portions of sample sheet 82 do not jeopardize sectioning the resulting block as in previously known molds. In embodiments of mold 10 wherein depression floor 22 is centrally inclined, sample sheet 82 is arranged substantially convex on depression floor 22, whereas sample tissue 84 is substantially inside sample recess 24. In an associated block 30 produced using mold 10, sample tissue 84 is embedded substantially inside sample protrusion 34, and therefore plains of sectioning of sample protrusion 34 to obtain slices of sample tissue 84 are generally more distant from sample sheet 82 compared to molds wherein sample sheet depression is not centrally inclined, thereby reducing the likelihood of undesired sectioning of the sample sheet.

FIG. 6A is an exploded schematic diagram of an embodiment of molding apparatus 60 comprising mold 10 and press 50, in use together with sample sheet 82. FIG. 6B schematically depicts a cross-section view of an embodiment of molding apparatus 60, having a sample sheet 82, carrying a sample tissue 84 adhered thereon, placed inside centrally-inclined depression floor 22. Press 50 presses sample sheet 82 and sample tissue 84 substantially into sample recess 24.

FIG. 7A is an exploded schematic diagram of an embodiment of molding apparatus 80 comprising mold 10 and press 70, in use together with sample sheet 82. FIG. 7B schematically depicts a cross-section view of an embodiment of molding apparatus 80, having a sample sheet 82, carrying a sample tissue 84 adhered thereon, placed inside sample sheet depression 18.

According to some embodiments, a block of an embedding material, embedding a sample tissue may be produced using molding apparatus 60 or molding apparatus 80. For example, a sample tissue 84 may be adhered to sample sheet 82 and sample sheet 82 may be placed substantially inside sample sheet depression 18 so that the face thereof carrying sample tissue 84 is facing mold 10 and sample tissue 84 is situated substantially inside sample recess 24. A small amount of liquid paraffin, enough to fill sample recess 24, is poured into sample recess 24. Press 50 or press 70 are pressed into sample sheet depression 18, thereby curving sample sheet 82 and pressing sample tissue 84 into sample recess 24 and submerging sample tissue 84 in the paraffin therein. Excess quantity of paraffin may be pressed out from sample recess 24 through major channels 64 and minor channels 66. After the small amount of paraffin solidifies, thereby capturing sample tissue 84, press 50 may be removed, and an additional amount of liquid paraffin may be poured into compartment 12 to produce a complete block such as block 30.

Some embodiments of molding apparatus 60 and molding apparatus 80 may be advantageous because in a block of embedding material such as block 30, produced using molding apparatus 60 or molding apparatus 80 and comprising sample tissue 84 therein, sample tissue 84 is necessarily arranged substantially confined to a plane, being adhered to sample sheet 82 and being confined by gap 62 or gap 68 respectively. Moreover, by considering the size of sample tissues that are expected to be embedded using molding apparatus 60 or molding apparatus 80, the size of gap 62 or gap 68 respectively may be configured. Accordingly, when employing molding apparatus 60 or molding apparatus 80 as described above, a sample tissue that is to be embedded, may not be squeezed at all, or may be squeezed to any desired extent, according to the thickness of the sample tissue compared to the size of gap 62 or gap 68, respectively. Further yet, foot protrusion 76 of press 70, causes sample tissue 84 to enter substantially into sample recess 24 by pressing onto and folding sample sheet 82 in a portion thereof into sample recess 24. Hence, a suitable separation is provided between sample tissue 84 that is relatively protruding into sample protrusion 34 of block 30, and sample sheet 82 which is necessarily embedded deeper inside block 30. As detailed above, the shape of sample sheet 82 inside block 30, dictated by the curvature of depression floor 22 and foot surface 56 or foot protrusion 76, increases the separation between sample tissue 84 that is relatively protruding into sample protrusion 34 of block 30, and sample sheet 82 which is necessarily embedded deeper inside block 30.

Figure 8A:
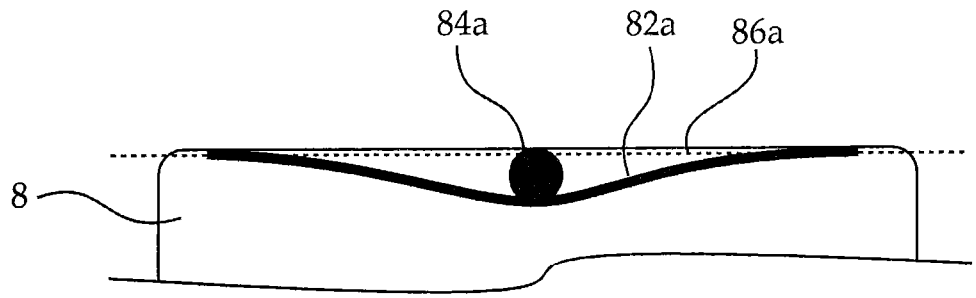
FIGS. 8A to 8D schematically depict, in a cross section view, blocks of an embedding material embedding inside a sample tissue adhered to a sample sheet, produced, respectively, by a mold of the prior art and by three molds according to the teachings herein.

FIGS. 8A to 8D schematically depict four blocks, respectively, of an embedding material embedding there inside sample tissue 84a adhered to sample sheet 82a, in a cross section view. Specifically, FIG. 8A schematically depicts a block 8 produced using a mold of the prior art such as mold 6 depicted in FIGS. 1A. A sectioning plain 86a indicates schematically a plain of sectioning the block with the sample tissue 84a inside to obtain a slice of the sample tissue suitable for inspection. Sectioning plain 86a includes not only a portion of sample tissue 84a but also a portion of sample sheet 82a, thereby demonstrating a potential disadvantage of a mold of the prior art compared to molds of the present invention.

Figure 8B:
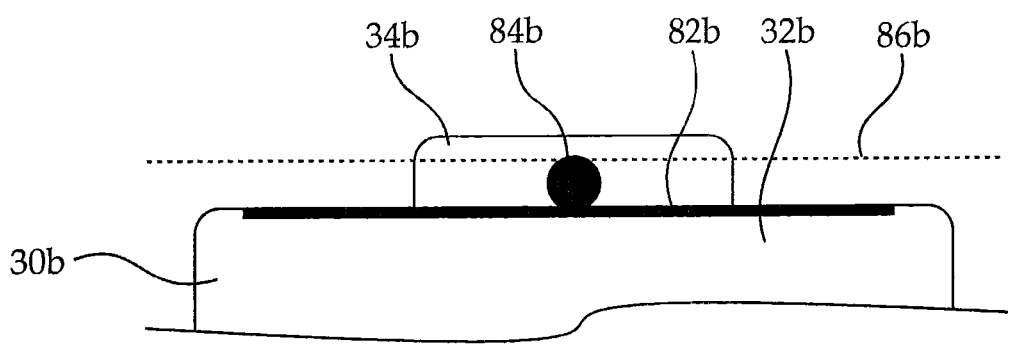

FIG. 8B depicts a block 30b of an embedding material, comprising a sample sheet protrusion 32b and a sample protrusion 34b, generated in a mold of the invention wherein depression floor 22 is not convex but is flat (outside the region of sample recess 24). Consequently, sample sheet 82b in FIG. 8B is substantially planar. A sectioning plain 86b indicates schematically a plain of sectioning the block with the sample tissue 84b inside to obtain a slice of the sample tissue suitable for inspection. Compared to sectioning performed in a block obtained from a mold of the prior art such as block 8 described above, sectioning plain 86b includes a smaller portion of the paraffin block, namely a portion corresponding to sample protrusion 34b. Moreover, sectioning plain 86b does not include any portion of sample tissue 84b, thereby diminishing a risk of obstructing the sectioning by the sample sheet.

Figure 8C:
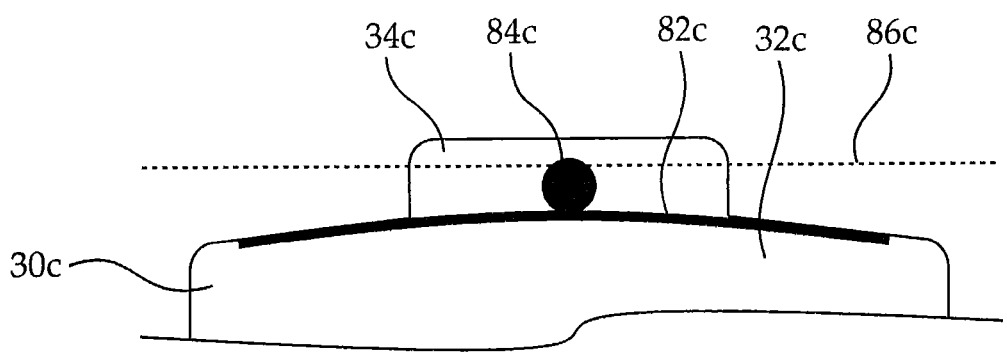

FIG. 8C depicts a block 30c of an embedding material, comprising a sample sheet protrusion 32c and a sample protrusion 34c, generated in a molding apparatus such as molding apparatus 60, with a mold 10 having a centrally inclined depression floor, and using press 50 (wherein foot surface 56 is convex with no protrusion). Consequently, sample sheet 82c in FIG. 8C is substantially convex, thereby distancing sample sheet 82c from the sectioning plain 86c even more, compared to block 30b in FIG. 8B.

Figure 8D:
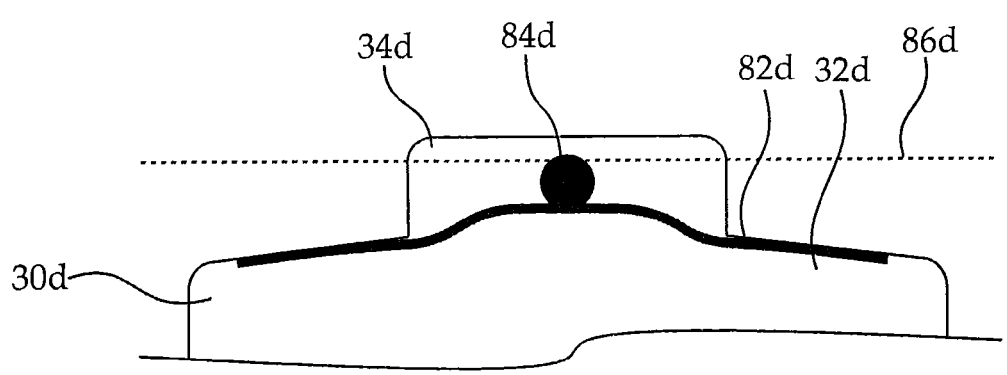

FIG. 8D depicts a block 30d of an embedding material, comprising a sample sheet protrusion 32d and a sample protrusion 34d, generated in a molding apparatus 80 comprising mold 10 and using press 70 (wherein foot surface 74 is convex with foot protrusion 76). Consequently, sample sheet 82d in FIG. 8D is substantially convex, and further penetrates into sample protrusion 34d due to foot protrusion 76, thereby distancing sample sheet 82d from the sectioning plain 86d even more, compared to block 30c in FIG. 8C.

Molding apparatuses 60 and 80 comprise mold 10 having depression floor 22 being concave, and a press 50 or press 70, respectively, with a convex foot surface 56 or foot surface 74, respectively. The curvature of foot surface 56 and foot surface 74 is equal or similar to the curvature of depression floor 22. This curvature confers two advantages to molding apparatuses 60 and 80. First, sample tissue 84, either when adhered to sample sheet 82 or when independently placed on a drop of embedding material in sample recess 24, is pushed towards sample recess floor 26. This reduces the labor required to expose sample tissue 84 when sectioning sample protrusion 34. Second, when sample sheet 82 is used to place a sample tissue 84 into sample recess 24, sample sheet 82 acquires the same curvature of depression floor 22 and foot surface 56 or foot surface 74. A curved sample sheet 82, in which the edges are more distant from the center carrying sample tissue 84, eliminates the risk of segments of sample sheet 82 being situated in planes of sectioning.

Figure 9B:
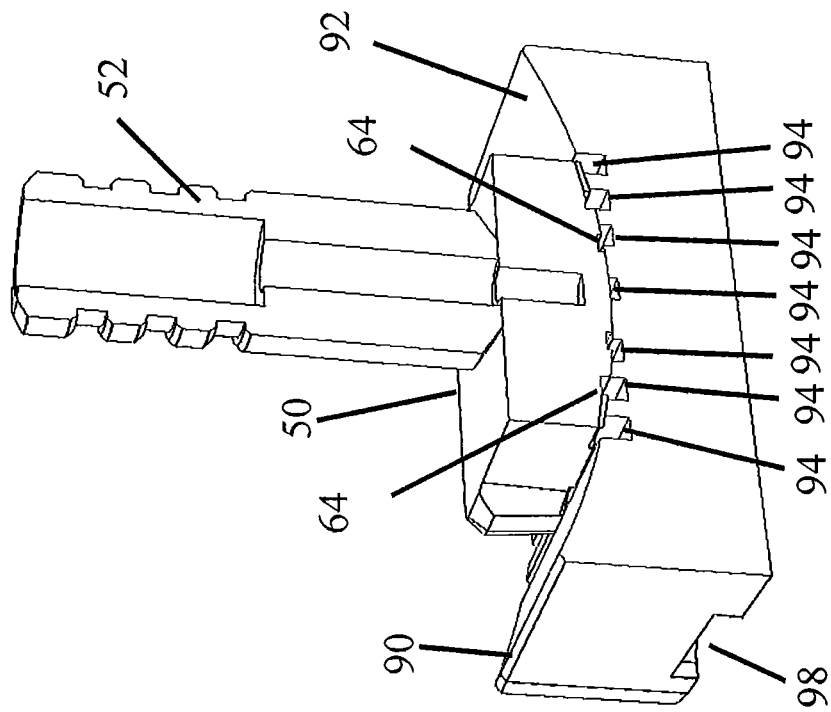
FIG. 9B schematically depicts the cleaning device of FIG. 9A with the press of FIG. 3A positioned thereon.
Figure 9A:
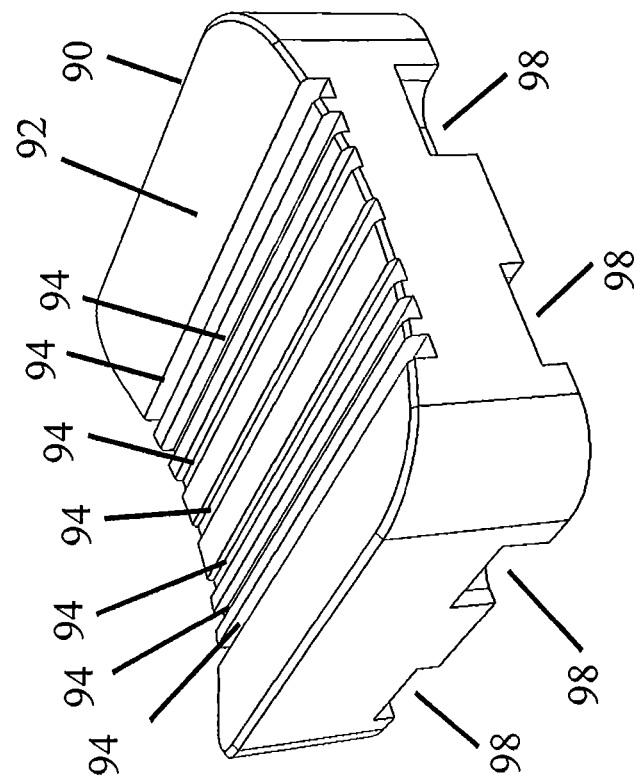
FIG. 9A schematically depicts an embodiment of a cleaning device for cleaning the press of FIG. 3A by heating.

FIG. 9A is a perspective schematic diagram of an embodiment of a cleaning device 90. Cleaning device 90 is configured to clean a press such as press 50 used for embedding a sample tissue in an embedding material inside a mold. Such cleaning is carried out by heating and melting residues of the embedding material left on the press. Cleaning device 90 comprises a cleaning surface 92, fitting in shape, at least partly, to foot surface 56 of press 50. Cleaning surface 92 is of the same curvature of foot surface 56. Cleaning surface 92 is configured to be heated, and to transfer heat towards foot surface 56 when press 50 is placed thereon. Due to the heating, residues of embedding material attached to foot surface 56 liquefy and detach from foot surface 56, potentially onto cleaning surface 92. Cleaning surface 92 comprises a cleaning device major channel 94 for draining liquid embedding material from cleaning surface 92. Cleaning device major channel 94 is at least partly open at cleaning surface 92 to drain liquid embedding material from foot cleaning surface 92. Cleaning device 90 further comprises on a bottom part thereof a cleaning device depression 98. Cleaning device depression 98 is configured to be attached to a solid base (not shown) when cleaning device 90 is in use or during storage, the base being configured to stabilize cleaning device 90 in place.

FIG. 9B is a schematic diagram of an embodiment of a cleaning device 90 and a press 50 positioned thereon, in a section view. Press 50 comprises at its bottom foot surface 56, which may become contaminated with residues of embedding materials, e.g. paraffin. Cleaning surface 92 is concave, optionally with the same curvature of foot surface 56, in order to maximize cleaning surface 92 and foot surface 56 interaction area thereby facilitating the cleaning process.

Figure 10A:
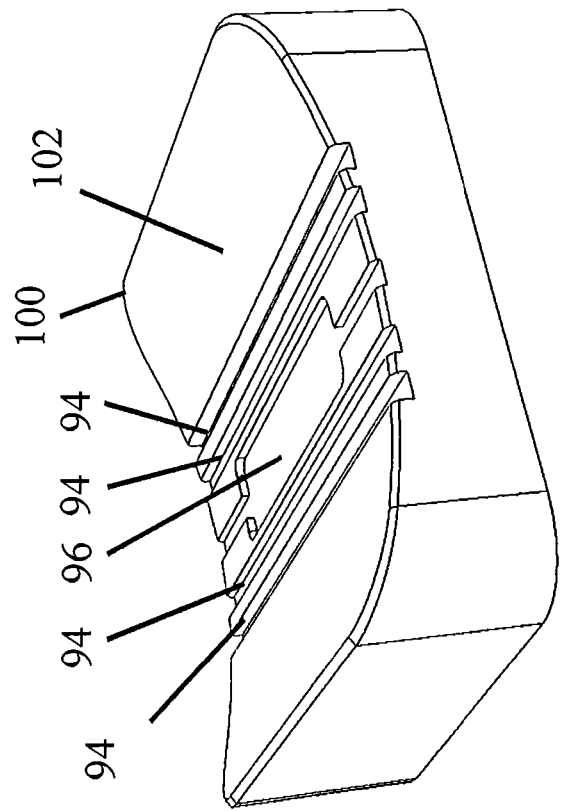
FIG. 10A schematically depicts an embodiment of a cleaning device for cleaning the press of FIG. 4A by heating, and FIG. 10B schematically depicts the cleaning device of FIG. 10A with the press of FIG. 4A positioned thereon.

FIG. 10A is a schematic diagram of an embodiment of a cleaning device 100, comprising a cleaning surface 102 and cleaning device major grooves 94. Cleaning device 100 is different from cleaning device 90, by further comprising a cleaning device central groove 96, configured to accept foot protrusion 76 of press 70 therein. Cleaning device 100 is thereby configured to clean a press such as press 70, by heating and melting residues of the embedding material left on the press.

Figure 10B:
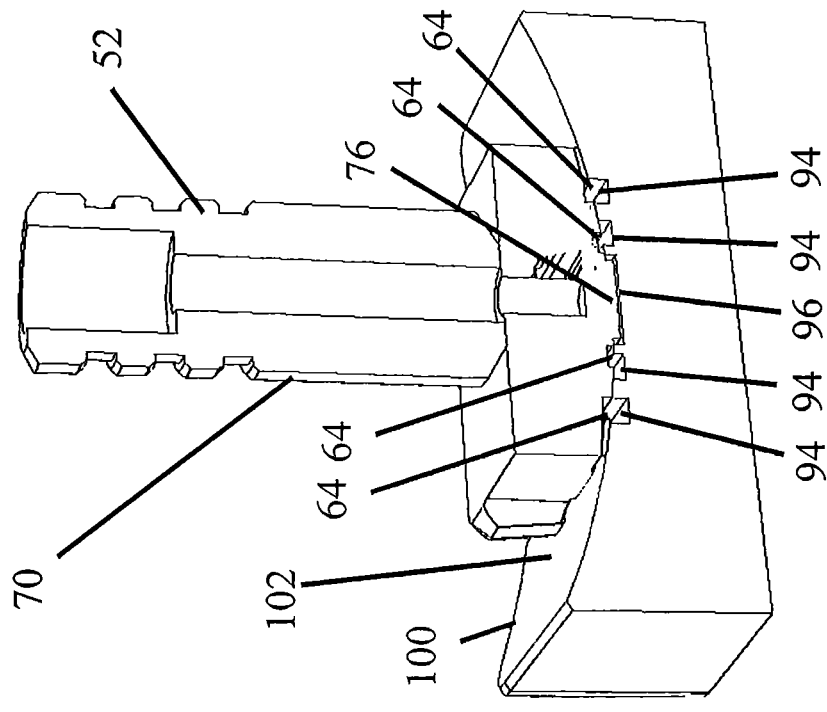

FIG. 10B is a schematic diagram of an embodiment of cleaning device 100 and a press 70 positioned thereon, in a section view. Press 70 comprises foot protrusion 76, which may become contaminated with residues of embedding materials, e.g. paraffin. Cleaning device central groove 96 receives therein, at least in part, foot protrusion 76.

According to some embodiments, cleaning devices 90 or 100 comprises cleaning surfaces 92 and 102, respectively, with a similar curvature of foot surface 56 or foot surface 74, respectively. The phrases "similar curvature" and "same curvature" are used interchangeably and define two or more faces, which are curved, wherein the surfaces may coincide, when brought to contact one another, at least along an areal portion thereof. For example, foot surface 56 and depression floor 22 may have the same or a similar curvature, foot surface 56 and cleaning surface 92 may have the same or a similar curvature, and depression floor 22 and cleaning surface 92 may have the same or a similar curvature.

According to some embodiments, cleaning surface 92 and cleaning surface 102 may be heated to enable melting residues of embedding material from a press placed thereon. According to some embodiments, cleaning surface 92 and cleaning surface 102 is not horizontal, when cleaning device 90 or cleaning device 100, respectively, is in use. According to some embodiments, cleaning device major groove 94 is not horizontal when cleaning device 90 or cleaning device 100, respectively, is in use. According to some embodiments, cleaning device central groove 96 is not horizontal when cleaning device 100 is in use. According to some embodiments, cleaning device central groove 96 is configured to accept, at least in part, foot protrusion 76, thereby increasing the contact area between cleaning device 100 and press 70 placed thereon. Cleaning surface 92, cleaning device major groove 94 and cleaning device central groove 96 may not be horizontal when in use to facilitate liquid embedding material removal from press 50 or press 70, on cleaning device 90 or cleaning device 100, respectively, by gravity.

Heating of cleaning surface 92 and cleaning surface 102, in cleaning device 90 and cleaning device 100, respectively, may be achieved by various methods. According to some embodiments cleaning surface 92 or cleaning surface 102 may be exposed to an external heat source, such as a heating lamp, a hotplate or any heated surface, before a press is placed thereon, or during a time a press is situated thereon. According to some embodiments cleaning surface 92 or cleaning surface 102 may be kept in a warm environment, such as an oven, before use or during use. According to some embodiments cleaning surface 92 or cleaning surface 102 may be kept in a warm liquid, such as in a water bath before use or during use. According to some embodiments cleaning surface 92 or cleaning surface 102 may be heated by being exposed to radiation such as microwave radiation or infra-red radiation. To be heated by an external heat source, in some embodiments, cleaning surface 92 or cleaning surface 102 may be capable of being heated by an external heat source, i.e. capable of substantially storing heat. In some embodiments, cleaning surface 92 and cleaning surface 102 withstands temperatures below 200° degrees Celsius.

In some embodiments, cleaning device 90 or cleaning device 100 may comprise an internal heat source, such as an electric heating coil for heating cleaning surface 92 or cleaning surface 102, respectively. In some embodiments the internal heat source may be powered by an external energy source, such as the electric grid, via e.g. an electric cord. In some embodiments the internal heat source may be powered by an internal source, such as a battery, via e.g. electric wiring, and the cleaning device may be portable.

Thus, according to an aspect of some embodiments there is provided a mold 10 for producing a biological tissue embedded in a block 30 of an embedding material. The mold comprises a compartment 12 configured for containing the embedding material, the compartment having a compartment floor 14 and at least one wall 16 extending upwards from the compartment floor. The compartment comprises at least one depression 18 extending downwards from the compartment floor, and the depression comprises a depression floor 22. At least one of the depression floor and compartment floor is curved at least along one direction, thereby being centrally inclined. The depression is configured for accepting a biological tissue at least partially therein, the mold being thereby configured for producing a block of an embedding material having at least one protrusion (32, 34), associated with the at least one depression, wherein the biological tissue is embedded at least partially in the protrusion.

According to some embodiments the compartment 12 has a non-symmetrical shape, substantially precluding rotational symmetry of the mold except for a trivial rotational symmetry of 360 degrees, the mold being thereby configured to produce a block of an embedding material without rotational symmetry except for the trivial rotational symmetry of 360 degrees. According to some embodiments the depression 18 has a substantially rectangular shape with one truncated corner 26, thereby precluding a rotational symmetry from the mold.

According to some embodiments the compartment further comprises a sample recess 24, extending downwards from the depression floor.

According to an aspect of some embodiments there is provided a molding apparatus comprising the mold of the invention and a sample sheet 82 configured to attach to a biological tissue 84 and hold the biological tissue thereon. The sample sheet is dimensioned to be positioned in the compartment and to be constrained to the position thereof, at least along one direction (in the horizontal plain), by the compartment. According to some embodiments the sample sheet is precluded by the compartment from lateral displacements. According to some embodiments the sample sheet is denied by the compartment from rotational displacements.

According to some embodiments the sample sheet is holding a sample tissue 84 thereon and is positioned in the compartment so that the biological tissue faces the depression floor (22, 26) and located at least partially within the at least one depression.

According to an aspect of some embodiments there is provided a molding apparatus (60, 80) comprising the mold of the invention and a press (50, 70). The molding apparatus is configured to press a biological tissue at least partially into the depression. The press comprises a handle 52 for gripping the press, and a foot (54, 72) comprising a non-planar foot surface (56, 74), the foot being configured to enter at least partially into the compartment.

According to some embodiments the compartment 12 of the mold comprises a sample recess 24 extending downwards from the depression floor and having a sample recess floor 26, and the foot comprises a foot protrusion 76 configured to enter at least partially into the sample recess when the press enters the compartment. According to some embodiments the biological tissue is a core biopsy sample wherein a gap 68 between the foot protrusion 76 and the sample recess floor when the press is fully entered into the compartment corresponds to a width of the core biopsy sample.

According to some embodiments the depression floor 22 of the mold is curved at least along one direction, thereby being centrally inclined. The foot surface (56, 74) of the press (50, 70) is curved at least along one direction, thereby being convex. The foot surface coincides with the depression floor at least along an areal surface portion thereof when the press enters the compartment.

According to some embodiments the foot of the press comprises a channel (64, 66, 58) configured to drain liquid embedding material when the press is pressed onto the compartment floor. According to some embodiments the channel comprises a groove (64, 66) extending between an edge of the foot surface and a central region of the foot surface, thereby being configured to drain liquid embedding material from the central region outwards towards the edge, or from a periphery of the foot surface towards a central region thereof, when the press enters the compartment. According to some embodiments the channel comprises a through hole extending from the foot surface upwards through the foot, thereby being configured to drain liquid embedding material from the foot surface upwards or from above the foot towards the foot surface.

According to an aspect of some embodiments there is provided a cleaning device (90, 100) configured to heat up a press (50, 70), the press being configured for pressing a sample tissue in a mold with an embedding material. The press comprises a foot (54, 72) having a foot surface (56, 74) and the cleaning device comprises a cleaning surface (92, 102) fitting in shape, at least partially, to the foot surface of the press. According to some embodiments the foot surface is substantially curved, and the cleaning surface has a substantially same curvature as the foot surface.

According to some embodiments the cleaning surface comprises channels 94, the channels being open at the cleaning surface, for draining liquid embedding material from the press.

According to some embodiments the cleaning device further comprises an internal heat source for heating the foot of the press. According to some embodiments the internal heat source is an electric heating coil. According to some embodiments the cleaning device is configured to receive energy from an external electric power source using an electric cord. According to some embodiments the cleaning device is configured to receive energy from an internal electric power source.

According to an aspect of some embodiments there is provided a method of embedding a biological tissue in a block of an embedding material, comprising providing a mold according to the teachings herein; placing a biological tissue in the compartment and at least partially inside the at least one depression, and employing an embedding material to produce a block of the embedding material inside the compartment wherein the biological tissue is embedded at least partially in a protrusion of the block corresponding to the at least one depression of the compartment.

According to some embodiments the method further comprises the steps of:

providing a sample sheet configured to attach to a biological tissue and hold the biological tissue thereon. The sample sheet is further dimensioned to be positioned in the compartment and to be constrained to the position thereof, at least along one direction, by the compartment;

attaching a biological tissue to the sample sheet, and positioning the sample sheet having the biological tissue attached thereto inside the compartment so that the biological tissue faces the depression floor and located at least partially within the at least one depression of the compartment.

According to some embodiments the method further comprises providing a press having foot with a non-planar foot surface wherein the foot is configured to insert at least partially into the compartment of the mold. The method further comprises pressing the press onto the compartment floor thereby inserting the biological tissue at least partially into the at least one depression, and thereby obtaining a block of the embedding material comprising the biological tissue embedded at least partially in the at least one protrusion of the block.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those features.

Although the invention is described in conjunction with specific embodiments thereof, it is evident that many alternatives, modifications and variations of these embodiments should be apparent to those skilled in the art. Accordingly, the invention is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A molding apparatus for producing a biological tissue embedded in a block of an embedding material, said molding apparatus comprising a mold comprising a compartment configured for containing said embedding material, said compartment having a compartment floor and at least one wall extending upwards from said compartment floor, and wherein said compartment comprises at least one depression extending downwards from said compartment floor, and wherein said depression comprises a depression floor, wherein at least one of said depression floor and compartment floor is curved at least along one direction, thereby being centrally inclined, the molding apparatus further comprising a sample sheet configured to attach to said biological tissue and hold said biological tissue thereon, said sample sheet being further dimensioned to be positioned in said compartment and to be constrained to said position thereof, at least along one direction, by said compartment, and wherein said depression is configured for accepting said biological tissue at least partially therein, thereby said molding apparatus being configured for producing a block of an embedding material having at least one protrusion associated with said at least one depression wherein said biological tissue, attached to said sample sheet, is embedded at least partially in said protrusion.

2. The molding apparatus of claim 1 wherein said compartment has a non-symmetrical shape, precluding rotational symmetry of said mold except for a trivial rotational symmetry of 360 degrees, said mold being thereby configured to produce a block of an embedding material without rotational symmetry except for the trivial rotational symmetry of 360 degrees.

3. The molding apparatus of claim 2 wherein said depression has a rectangular shape with one truncated corner, thereby precluding a rotational symmetry from said mold.

4. The molding apparatus of claim 1 wherein said compartment further comprises a sample recess, extending downwards from said depression floor.

5. The molding apparatus of claim 1 wherein said sample sheet is precluded by the compartment from lateral displacements.

6. The molding apparatus of claim 1 wherein said sample sheet is precluded by the compartment from rotational displacements.

7. The molding apparatus of claim 1 wherein said sample sheet is holding a sample tissue thereon and is positioned in said compartment so that said biological tissue faces said depression floor and located at least partially within said at least one depression.

8. The molding apparatus of claim 1 further comprising a press, said molding apparatus being configured to press a biological tissue at least partially into said depression, said press comprising a handle for gripping said press, and a foot comprising a non-planar foot surface, said foot being configured to enter at least partially into said compartment.

9. The molding apparatus of claim 8 wherein said compartment of said mold comprises a sample recess extending downwards from said depression floor and having a sample recess floor, and said foot comprises a foot protrusion configured to enter at least partially into said sample recess when said press enters said compartment.

10. The molding apparatus of claim 9 wherein said biological tissue is a core biopsy sample wherein a gap between said foot protrusion and said sample recess floor when said press is fully entered into said compartment corresponds to a width of said core biopsy sample.

11. The molding apparatus of claim 8 wherein said depression floor of said mold is curved at least along one direction, thereby being centrally inclined and said foot surface of said press is curved at least along one direction thereby being convex, so that said foot surface coincides with said depression floor at least along an areal surface portion thereof when said press enters said compartment.

12. The molding apparatus of claim 9 wherein said foot of said press comprises a channel configured to drain liquid embedding material when said press is pressed onto said compartment floor.

13. The molding apparatus of claim 12 wherein said channel comprises a groove extending between an edge of said foot surface and a central region of said foot surface, thereby being configured to drain liquid embedding material from said central region outwards towards said edge, or from a periphery of said foot surface towards a central region thereof, when said press enters said compartment.

14. The molding apparatus of claim 12 wherein said channel comprises a through hole extending from said foot surface upwards through said foot, thereby being configured to drain liquid embedding material from said foot surface upwards or from above said foot towards said foot surface.

15. The molding apparatus of claim 8 further comprising a cleaning device configured to heat up said press, wherein said cleaning device comprises a cleaning surface fitting in shape, at least partially, to said foot surface of said press.

16. The molding apparatus of claim 15 wherein said foot surface is curved, and said cleaning surface has a same curvature as said foot surface.

17. The molding apparatus of claim 15 wherein said cleaning surface comprises channels, said channels being open at said cleaning surface, for draining liquid embedding material from said press.

18. The molding apparatus of claim 15 wherein said cleaning device further comprises an internal heat source for heating said foot of said press.

19. The molding apparatus of claim 18 wherein said internal heat source is an electric heating coil.

20. The molding apparatus of claim 18 wherein said cleaning device is configured to receive energy from an external electric power source using an electric cord.

21. The molding apparatus of claim 18 wherein said cleaning device is configured to receive energy from an internal electric power source.

22. A method of embedding a biological tissue in a block of an embedding material, comprising:
    providing the molding apparatus of claim 1;
    attaching the biological tissue to the sample sheet;
    positioning the sample sheet having the biological tissue thereon inside the compartment so that the biological tissue faces the depression floor and located at least partially within the at least one depression of the compartment, and
    employing an embedding material to produce the block of the embedding material inside the compartment wherein the biological tissue is embedded at least partially in a protrusion of the block corresponding to the at least one depression of the compartment.

23. The method of claim 22 further comprising the steps of:
    providing a press having foot with a non-planar foot surface wherein the foot is configured to insert at least partially into the compartment of the mold; and
    pressing the press onto the compartment floor thereby inserting the biological tissue at least partially into the at least one depression, and thereby obtaining a block of the embedding material comprising the biological tissue embedded at least partially in the at least one protrusion of the block.

* * * * *